United States Patent [19]

Fujii et al.

[11] 4,454,338
[45] Jun. 12, 1984

[54] AMIDINE COMPOUND

[75] Inventors: Setsuro Fujii, Toyonaka; Toshiyuki Okutome, Tokyo; Toyoo Nakayama; Takashi Yaegashi, both of Funabashi; Masateru Kurumi, Narita, all of Japan

[73] Assignee: Torii & Co., Ltd., Tokyo, Japan

[21] Appl. No.: 300,534

[22] Filed: Sep. 9, 1981

[30] Foreign Application Priority Data

Sep. 16, 1980 [JP] Japan .................. 55-128269
Apr. 28, 1981 [JP] Japan .................. 56-64942

[51] Int. Cl.$^3$ .................. C07C 101/00; C07C 101/48
[52] U.S. Cl. .................. 560/34; 560/17; 560/12; 560/73; 560/49; 560/37; 560/20; 560/86; 560/67; 560/107; 260/465 D; 424/304; 424/309; 424/282
[58] Field of Search .................. 560/34, 108, 160

[56] References Cited

U.S. PATENT DOCUMENTS 4,021,472  5/1977  Fujii et al. .................. 560/34

FOREIGN PATENT DOCUMENTS 1905813  3/1970  Fed. Rep. of Germany ........ 560/34

OTHER PUBLICATIONS

Wagner et al., Pharmazie, vol. 32 (1977), H12, pp. 761–763.
Takada et al., Immunology, vol. 34 (1978), pp. 509–515.
Wagner et al., (I), Pharmazie, 28(5) (1973), 293–296.

*Primary Examiner*—Bernard Helfin

*Attorney, Agent, or Firm*—Beveridge, DeGrandi & Kline

[57] ABSTRACT

Amidino compounds represented by the formula

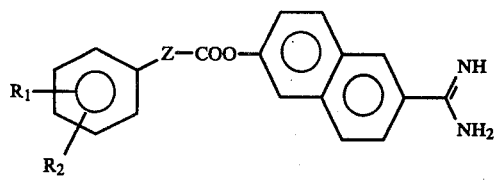

and pharmaceutically acceptable acid addition salts thereof are novel compounds and are useful as powerful antitrypsine, antiplasmin, antikallikrein and antithrombin agents. Having strong anti-C1 (C1r̄, C1s̄) activities and an anticomplement activity, they are also useful as anticomplement agents. These amidino compounds are prepared by usual esterification of carboxylic acid compounds represented by the formula

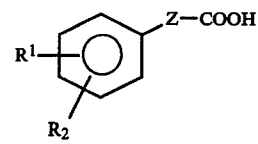

with 6-amidino-2-naphthol and, if necessary, can be transformed into pharmaceuticlly acceptable acid addition salts thereof.

1 Claim, No Drawings

AMIDINE COMPOUND

This invention relates to novel amidino compounds (I) of the formula

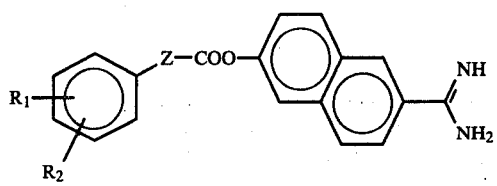

having strong anti-trypsin, anti-plasmin, anti-kallikrein and anti-thrombin activities and also an anti-complement activity, and to a process for producing said novel compounds.

6-Amidino-2-naphthol (III),

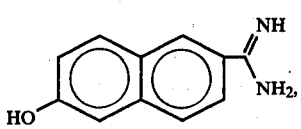

is known to be a substance which inhibits trypsin, plasmin and thrombin [G. Wagner et al., Pharmazie, 32, H 12, 761–763 (1977)] and Leupeptin is known to be a substance having an anti-complement activity [Y. Takada et al., Immunology 34, 509–515 (1978)]. The present compound (I) has anti-trypsin, antiplasmin and anti-thrombin activities for stronger than those of 6-amidino-2-naphthol and an anti-complement activity stronger than that of Leupeptin. This means that with respect to anti-trypsin, anti-plasmin, anti-kallikrein, anti-thrombin and anti-complement activities, the same pharmaceutical effect is obtained with a smaller dose of the compound (I) than with a dose of 6-amidino-2-naphthol (III) or leupeptin.

An object of this invention is to provide a pharmaceutically useful novel amidino compounds represented by the formula (I)

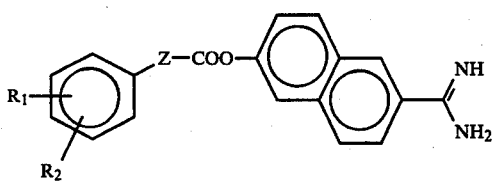

and pharmaceutically acceptable acid addition salts thereof.

Another object of this invention is to provide powerful anti-trypsin, anti-plasmin, anti-kallikrein and anti-thrombin agents.

A still another object of this invention is to provide powerful anti-complement agents.

A further object of this invention is to provide a process for producing said novel amidino compounds.

The present compound (I) can be produced by subjecting a carboxylic acid compound represented by the following formula (II) or a reactive intermediate thereof and 6-amidino-2-naphthol of the following formula (III) to usual esterification:

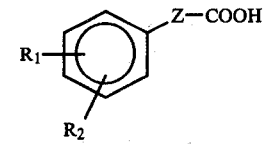

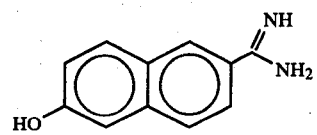

This invention relates to an amidino compound represented by the formula (I)

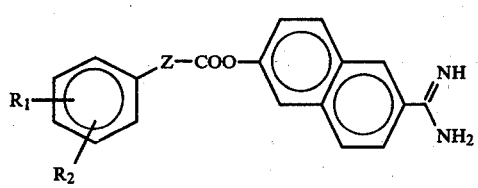

In formulas of the amidino compound (I) and the carboxylic acid compound (II) described in this Specification and the appended Claims, Z represents $-(CH_2)_a-$,

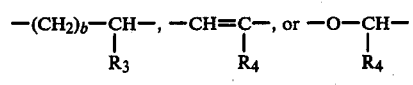

wherein a is 0, 1, 2 or 3, b is 0, 1 2, $R_3$ is a straight or branched chain alkyl group of 1 to 4 carbon atoms or a cycloalkyl group of 3 to 6 carbon atoms, $R_4$ is a hydrogen atom or a straight or branched chain alkyl group of 1 to 4 carbon atoms. Examples of the carboxylic acid compound (II) wherein Z is as defined above include benzoic acid, phenylacetic acid, phenylpropionic acid, phenylbutyric acid, α-methylphenylacetic acid, α-cyclohexylphenylacetic acid, α-ethylphenylacetic acid, α-methylphenylpropionic acid, α-ethylphenylpropionic acid, α-methylphenylbutyric acid, cinnamic acid, α-methylcinnamic acid, α-ethylcinnamic acid, phenoxyacetic acid, α-methylphenoxyacetic acid, or substituted compounds of these acids, and examples of the amidino compound (I) wherein Z is as defined above 6-amidino-2-naphthyl esters of the above acids.

$R_1$ and $R_2$, which may be the same or different, represent each a hydrogen atom, a straight or branched chain alkyl group of 1 to 4 carbon atoms, $-O-R_5$, $-S-R_5$, $-COOR_5$, $-COR_6$, $-O-COR_7$, $-NHCOR_7$,

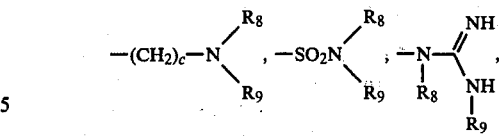

$NO_2$, CN, halogen, $CF_3$, methylenedioxy, or

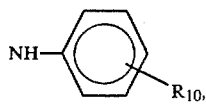

wherein c is 0, 1 or 2; $R_5$ is a hydrogen atom, linear or branched chain alkyl group of 1 to 4 carbon atoms, or benzyl group; $R_6$ is a hydrogen atom or straight or branched chain alkyl group of 1 to 4 carbon atoms; $R_7$ is a straight or branched chain alkyl group of 1 to 4 carbon atoms; $R_8$ and $R_9$, which may be the same or different, are each a hydrogen atom, straight or branched chain alkyl group of 1 to 4 carbon atoms, or amino radical protecting group; and $R_{10}$ is a hydrogen atom, dimethyl or $CF_3$. The straight or branched chain alkyl groups of 1 to 4 carbon atom include methyl, ethyl, n-propyl, isopropyl, n-butyl, isobutyl and tert-butyl.

Examples of $R_1$ and $R_2$ include hydrogen, methyl, ethyl, n-propyl, n-butyl, tert-butyl, hydroxy, methoxy, ethoxy, n-propyloxy, n-butyloxy, benzyloxy, mercapto, methylthio, ethylthio, carboxy, methoxycarbonyl, ethoxycarbonyl, butoxycarbonyl, formyl, acetyl, ethylcarbonyl, guanidino, N-methylguanidino, N-n-butyl-guanidino, acetoxy, propionyloxy, butyryloxy, acetamino, propionyl amino, butyrylamino, amino, dimethylamino, dibutylamino, aminomethyl, benzyloxycarbonylaminomethyl, sulfamyl, dimethylsulfamyl, nitro, cyano, fluorine, chlorine, bromine, iodine, trifluoromethyl, methylenedioxy, phenylamino, 3,4-dimethylphenylamino, and 3-trifluoromethylphenylamino.

The compound (I) of this invention can be produced by the reaction between a carboxylic acid compound of the formula (II) or a reactive intermediate thereof and 6amidino-2-naphthol of the formula (III) or preferably an acid addition salt thereof. The reactive intermediates, as herein referred to, include acid halides and acid anhydrides commonly used in the dehydration condensation and the reactive intermediates formed by reacting dicyclohexyl carbodiimide (DCC), diphenylphosphorylazide (DPPA), or the like with a carboxylic acid derivative.

The process for producing the present compound is described below in detail.

The present compound (I) can be prepared by dissolving or suspending a carboxylic acid compound (II) in an organic solvent such as dimethylformamide, pyridine, or the like, then allowing the compound (II) to react with an carboxylic acid activator such as dicyclohexylcarbodiimide (DCC), diphenylphosphoryl azide (DPPA), or the like, which is usually used as dehydration-condensation agent, and adding 6-amidino-2-naphthol (III) or preferably an acid addition salt thereof to the reaction product.

For instance, when DCC is used as the dehydration-condensation agent, a carboxylic acid derivative (II) is added to a solvent such as pyridine, then the mixture is stirred with cooling in ice or at room temperature for 10 minutes to 2 hours, then 6-amidino-2-naphthol (III) is added, and the mixture is further stirred at a temperature between −30° and 80° C., preferably at room temperature, for 3 to 5 hours to complete the reaction, though it is not objectionable to continue the reaction overnight. Dicyclohexylurea (DCU) precipitates out of the reaction mixture, while the present compound (I) either precipitates with DCU or remains dissolved in the solvent. In the former case, both precipitates are collected by filtration, then suspended in a suitable solvent such as dimethylformamide or the like and the mixture is filtered to remove insoluble DCU. After adding to the filtrate a solvent such as ethyl ether, ethyl acetate, acetone or the like, the precipitate is collected by filtration to obtain the present compound (I). Alternatively, the combined precipitate of DCU and the present compound (I) is collected by filtration, then added to a suitable solvent such as dimethylformamide, water or the like to remove insoluble DCU by filtration, the filtrate is added to a saturated aqueous sodium hydrogencarbonate solution to obtain the present compound (I) in the form of carbonate. In the latter case, where the present compound remains dissolved in the reaction mixture, DCU is removed by filtration and the filtrate is admixed with a solvent such as ethyl ether, acetone, ethyl acetate, or the like to obtain the present compound (I).

In another process, when it is intended to use an acid halide as a reactive intermediate of a carboxylic acid derivative (II), the latter derivative (II) is allowed to react with an acid halogenation agent such as $SOCl_2$, $SOBr_2$, $PCl_5$ or the like to synthesize an acid halide represented by the formula (IV)

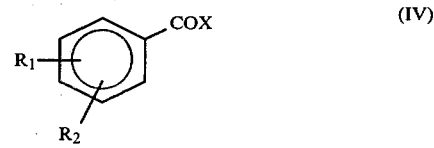

wherein $R_1$ and $R_2$ are as defined above and X represents a halogen atom. The acid halide is added to a solution of 6-amidino-2-naphthol (III), preferably in the form of an acid addition salt, dissolved in dimethylformamide, pyridine, dimethyl sulfoxide or the like and allows to react in the presence of a dehydrohalogenation agent. The dehydrohalogenation agents which can be used include inorganic bases such as potassium carbonate, sodium carbonate, sodium hydroxide and the like and organic bases such as triethylamine, pyridine, dimethylaniline and the like. Of these bases, pyridine is preferred. Although the reaction proceeds readily at a temperature in the range of −30° to 80° C., it is preferable for the purpose of avoiding side reactions to conduct the reaction in the early stage under ice cooling and then at room temperature. The reaction is complete in 2 to 5 hours, though the reaction mixture can be left overnight. After completion of the reaction, the reaction mixture is treated in a customary manner. For instance, when pyridine was used as the reaction medium, a solvent such as ethyl ether or ethyl acetate is added to the reaction mixture to precipitate a solid reaction product which is then recrystallized from a suitable solvent such as a methanol-ethyl ether mixture to obtain the present compound (I).

Further, if desired, the present compound (I) can be prepared in the corresponding reduced form by the reduction of a suitable compound of formula (I) by use of a suitable reducing agent. For example, a compound of formula (I) having a nitro group is converted into a compound of formula (I) having an amino group by the reduction. It is also possible to convert a cinnamic acid ester derivative having a double bond into a phenylpropionic acid derivative.

Still further, if desired, the present compound can be obtained by the removal of protective groups of amino, hydroxyl, and carboxyl groups. The protective groups, as herein referred to, include those which are commonly used, such as, for example, benzyloxycarbonyl, tert-butoxycarbonyl, benzyl and tert-butyl groups. For instance, a compound having an aminomethyl group is obtained by the removal of the protective group from a compound having a benzyloxycarbonylaminomethyl group and a compound having a hydroxyl group is obtained from a compound having a benzyloxy group.

If necessary, acid addition salts of the present compound may be prepared in a customary manner. For instance, carbonate of the present compound is dissolved or suspended in a solvent such as methanol, DMF or the like and the carbonate is allowed to dissolve by the addition of an acid such as methanesulfonic acid, hydrochloric acid or the like. To the resulting solution is added a solvent such as ethyl ether, ethyl acetate or the like to obtain a corresponding acid addition salt. Acids which can be used are pharmaceutically acceptable ones including inorganic acids such as hydrochloric acid, sulfuric acid and phosphoric acid and organic acids such as acetic acid, lactic acid, citric acid, methanesulfonic acid, succinic acid, fumaric acid and maleic acid.

The present compound and the pharmaceutically acceptable acid addition salt thereof possess powerful inhibitory activities against proteases, that is, trypsin, plasmin, kallikrein and thrombin and are effective as an anti-trypsin agent for the treatment of pancreatitis, as an anti-plasmin or anti-kallikrein agent for hemorrhagic diseases, and as an anti-thrombin agent for thrombus.

With respect to the above-mentioned proteases, their roles in a living body, the relationship to the diseases, the clinical significance of these protease inhibitors and the significance of the tests herein performed are explained below.

I. Trypsin: Trypsin is a protease existing originally in the form of proenzyme trypsinogen in the pancrease and the proenzyme is secreted into the small intestine where it is transformed into trypsin by activation with enterokinase existing therein. Trypsin has a role as one of digestive enzymes. If the trypsinogen is activated by any chance in the pancreas to form tryspin, the pancreas tissue will be injured to manifest clinically the symptoms of pancreatitis. In fact, it is known that in an experiment using rat as test animal, when trypsin is injected conversely into the pancreas, the onset of intense pancreatitis is observed but the disease is cured by the administration of a trypsin inhibitor. From this fact, it is presumable that the present compound having a strong trypsin inhibitory activity is useful as an anti-trypsin agent which is clinically effective for the treatment of pancreatitis.

II. Plasmin: Plasmin is an enzyme existing in the blood, usually in the form of proenzyme plasminogen which is converted to plasmin by the activation with a plasminogen tissue activator such as urokinase. This enzyme acts reversely to the action of thrombin, that is, it acts to dissolve fibrin. For this reason, plasmin plays an important role in securing blood flow through capillaries. However, when this enzyme become abnormally activated for some reason, it causes hemorrhagic diseases. This enzyme participates also in inflammation, increasing the vascular permeability and causing edema or the like. Therefore, an inhibitor for this enzyme is useful as a drug to treat hemorrhagic diseases and inflammation.

III. Kallikrein: Kallikrein is an enzyme widely distributed in blood and other organs and glands, usually in the form of its precursor prekallikrein which is activated with Hageman factor or other proteases. This enzyme participates in the hypotensive kallikrein-kinin system which counteracts the hyper tensive renin-angiotensin system and plays an important role in the control of blood pressure. This enzyme participates also in exogenous coagulation system. Further, kallikrein originated from organs or glands plays an important role in the improvement of local circulation. However, an abnormal activation, particularly an abnormal local activation, of this enzyme causes an insufficiency of local circulation due to the exaggeration of coagulation system, causing inflammation, ulcer, or the like. Therefore, a kallikrein inhibitor is useful for the control of blood pressure and as a drug for the treatment of inflammation or ulcer.

IV. Thrombin: Thrombin is known as an enzyme having a blood coagulating activity. In normal state, thrombin is formed by the activation of prothrombin in the blood when the vascular wall is injured. Thrombin acts to decompose the fibrinogen in the blood into fibrin. The resulting fibrin deposits on the injured part of vascular wall to prevent plasma components from transudation and simultaneously to promote the restoration of tissues. However, when the coagulation system is abnormally activated for some reason, a large number of fine thrombic are formed in capillaries throughout the entire body. Therefore, the present compound is useful as a drug for the treatment of such a disease.

The present compound and its pharmaceutically acceptable acid addition salts possess a strong C1 esterase ($\overline{C1r}$, $\overline{C1s}$) inhibitory activity, an ability of inhibiting the complement mediated hemolysis, and a therapeutic activity against the Forssman shock in which the activation of the complement system caused by an immune complex is said to play an important role. This indicates that the present compound is useful as an anti-complement agent effective for the treatment of allergic diseases such as nephritis associated with the complement.

The role of complement in the living body, the interrelation between a disease and the complement, the clinical significance of inhibitor, and the significance of tests (inhibition of $\overline{C1r}$, $\overline{C1s}$, complement mediated hemolysis, and Forssman shock) performed by the present inventors are described below.

Anti-complement activity:

(1) $\overline{C1r}$, $\overline{C1s}$

The complement is one of the serum components and comprises 9 components of C1 to C9. C1 is separated into 3 subcomponents of C1q, C1/r and C1s. $\overline{C1s}$ and $\overline{C1r}$ mean activated C1s and activated C1r, respectively. The complement was thought at first to perform a part of the infection protective process of living body, since it shows bacteriolysis, but recently an intimate relation to the immunity has been evident. It was shown that the complement is activated by the immune complex progressively from C1 to C9 and exhibits cytolysis or hemolysis at the final stage (activation of C9). It was also disclosed that the fragments (e.g. C3a, C5a) liberated in the course of activation of the complement system exaggerate the vascular permeability and promote the chemotaxis of polymorphonuclear leucocytes or immune adherence. Since that time, the interrelationship between the abnormal activation of complement and various diseases, particularly immune diseases, has been extensively investigated and, as the result, the intimate association of autoimmune diseases with the complement is beginning to be disclosed. Examples of the autoimmune diseases caused by the abnormal activation of complement include autoimmune hemolytic anemia, autoimmune thrombocytopenia, leukopenia, glomerulonephritis, systemic lupus erythematosus, serum sickness and periarteritis nodosa. It is expectable to cure such diseases by inhibiting the activation of complement or inhibiting the activated complement in an early stage. The present inventors examined the C1 esterase inhibitory effect of the present compound by using C1 esterase as target enzyme and, in addition, the influence of the present compound on the complement system to estimate the usefulness of the present compound as a drug for the treatment of autoimmune diseases.

(2) Complement mediated hemolysis:

The complement mediated hemolysis is widely used as a means to determine the titration of complement. The principle of this method is based on the fact that hemolysis is caused by the activation of complement, when the latter is added to a complex (immune complex) of erythrocytes and the antibody thereof. The degree of hemolysis varies in proportion to the amount of complement added. Therefore, when a known amount of complement admixed with a C1 esterase inhibitor is used, the hemolysis must be suppressed in proportion to the inhibitory activity. The present compound having C1 esterase inhibitory activity showed strong inhibition of complement mediated hemolysis as shown hereinafter.

(3) Forssman shock:

Quite different from other animals, guinea pig has on the surface of its organs a specific antigen called Forssman antigen which specifically reacts with the antibody of sheep erythrocyte. Forssman shock is based on the above principle and is a shock caused by the administration of antibody of sheep erythrocyte to a guinea pig. The Forssman shock was investigated in detail by many researchers and it was definitely shown that this shock is a model case where the complement plays the principal part and that the shock is associated with a classical pathway in which the complement system is activated progressively starting from C1. Since the participation of complement in autoimmune diseases has been established, the Forssman shock can be said to be a useful means for testing a drug for autoimmune diseases. A drug effective for the treatment of Forssman shock is useful as a drug of autoimmune diseases.

[Anti-trypsin, anti-plasmin, anti-kallikrein and anti-thrombin activities]

The anti-trypsin, anti-plasmin, anti-kallikrein and anti-thrombin activities were determined according to the method of Muramatsu et al. [M. Muramatsu, T. Onishi, S. Makino, Y. Hayashi and S. Fujii, J. of Biochem., 58, 214 (1965)]. The results were as shown in Table 1. The data summarized in Table 1 are expressed in terms of molar concentration ($ID_{50}$) of the test compound which inhibits 50% of the activity of each enzyme to hydrolyze TAME (tosylalginine methyl ester). The compound No. corresponds to the compound number shown in Examples. The figure in parentheses shows the percentage inhibition at a concentration of the compound of $1 \times 10^{-5}$M.

TABLE 1

| Compound No. | Trypsin | Plasmin | Kallikrein | Thrombin |
|---|---|---|---|---|
| 1 | $3 \times 10^{-6}$ | $2 \times 10^{-6}$ | $3 \times 10^{-5}$ | $5 \times 10^{-6}$ |
| 2 | (38) | $>10^{-5}$ | $>10^{-5}$ | $>10^{-5}$ |
| 3 | $2 \times 10^{-6}$ | $4 \times 10^{-6}$ | 38 | $4 \times 10^{-6}$ |
| 4 | $1 \times 10^{-6}$ | $5 \times 10^{-7}$ | $8 \times 10^{-6}$ | $2 \times 10^{-5}$ |
| 5 | $3 \times 10^{-7}$ | $2 \times 10^{-6}$ | $9 \times 10^{-6}$ | $3 \times 10^{-6}$ |
| 7 | | $3 \times 10^{-6}$ | 46 | $3 \times 10^{-6}$ |
| 8 | $4 \times 10^{-8}$ | (17) | (43) | (29) |
| 9 | $4 \times 10^{-8}$ | (48) | (19) | (20) |
| 10 | $2 \times 10^{-7}$ | $5 \times 10^{-5}$ | (31) | $4 \times 10^{-6}$ |
| 11 | $3 \times 10^{-7}$ | (36) | (21) | $7 \times 10^{-6}$ |
| 12 | (24) | (40) | $>10^{-5}$ | $>10^{-5}$ |
| 13 | $4 \times 10^{-7}$ | $2 \times 10^{-6}$ | (24) | (39) |
| 14 | $3 \times 10^{-7}$ | $5 \times 10^{-7}$ | NE | $3 \times 10^{-6}$ |
| 15 | $3 \times 10^{-6}$ | $1 \times 10^{-6}$ | (38) | $2 \times 10^{-6}$ |
| 16 | $3 \times 10^{-6}$ | $5 \times 10^{-7}$ | (31) | (38) |
| 17 | $4 \times 10^{-6}$ | $2 \times 10^{-6}$ | (23) | |
| 18 | $1 \times 10^{-5}$ | $3 \times 10^{-6}$ | $>10^{-5}$ | $2 \times 10^{-6}$ |
| 19 | (47) | $3 \times 10^{-6}$ | (11) | $2 \times 10^{-6}$ |
| 20 | $6 \times 10^{-8}$ | (27) | (31) | $>10^{-5}$ |
| 21 | $6 \times 10^{-7}$ | | $1 \times 10^{-5}$ | $>10^{-5}$ |
| 22 | $4 \times 10^{-6}$ | $4 \times 10^{-6}$ | $3 \times 10^{-6}$ | (26) |
| 23 | $2 \times 10^{-5}$ | $2 \times 10^{-5}$ | $1 \times 10^{-4}$ | $1 \times 10^{-5}$ |
| 24 | $3 \times 10^{-7}$ | $2 \times 10^{-5}$ | $5 \times 10^{-5}$ | $6 \times 10^{-5}$ |
| 25 | $3 \times 10^{-6}$ | $3 \times 10^{-6}$ | $1 \times 10^{-4}$ | $6 \times 10^{-5}$ |
| 27 | $2 \times 10^{-8}$ | $3 \times 10^{-7}$ | $5 \times 10^{-6}$ | $3 \times 10^{-6}$ |
| 28 | $6 \times 10^{-7}$ | $6 \times 10^{-7}$ | (20) | (17) |
| 29 | $1 \times 10^{-5}$ | $2 \times 10^{-6}$ | (42) | $2 \times 10^{-6}$ |
| 30 | $2 \times 10^{-6}$ | $2 \times 10^{-6}$ | (41) | $4 \times 10^{-6}$ |
| 31 | $4 \times 10^{-6}$ | $4 \times 10^{-7}$ | $>10^{-5}$ | $3 \times 10^{-7}$ |
| 32 | $2 \times 10^{-6}$ | $3 \times 10^{-6}$ | (26) | $4 \times 10^{-6}$ |
| 33 | $8 \times 10^{-6}$ | $3 \times 10^{-6}$ | (13) | (40) |
| 48 | $5 \times 10^{-6}$ | $2 \times 10^{-6}$ | $>10^{-5}$ | (43) |
| 49 | $2 \times 10^{-6}$ | $4 \times 10^{-6}$ | 29 | (17) |
| 51 | $1 \times 10^{-5}$ | $6 \times 10^{-6}$ | $>10^{-5}$ | (35) |
| 52 | (33) | $>10^{-5}$ | $>10^{-5}$ | $>10^{-5}$ |
| 57 | $5 \times 10^{-6}$ | $3 \times 10^{-6}$ | $5 \times 10^{-5}$ | $1 \times 10^{-5}$ |
| 58 | $2 \times 10^{-6}$ | $5 \times 10^{-7}$ | $>10^{-5}$ | (22) |
| 59 | $1 \times 10^{-7}$ | $6 \times 10^{-7}$ | $1 \times 10^{-6}$ | $6 \times 10^{-6}$ |

TABLE 1-continued

| Compound No. | Trypsin | Plasmin | Kallikrein | Thrombin |
|---|---|---|---|---|
| 60 | $3 \times 10^{-7}$ | $6 \times 10^{-7}$ | $3 \times 10^{-6}$ | (25) |
| 62 | $3 \times 10^{-6}$ | $2 \times 10^{-6}$ | $>10^{-5}$ | (24) |
| 63 | $2 \times 10^{-6}$ | $8 \times 10^{-6}$ | $4 \times 10^{-6}$ | $>10^{-5}$ |
| 64 | $2 \times 10^{-6}$ | $1 \times 10^{-5}$ | $4 \times 10^{-6}$ | $>10^{-5}$ |
| 66 | $6 \times 10^{-6}$ | $5 \times 10^{-7}$ | $>10^{-5}$ | (21) |
| 68 | $>10^{-5}$ | $>10^{-5}$ | $>10^{-5}$ | $1 \times 10^{-5}$ |
| 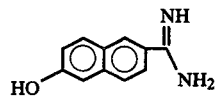 | $>10^{-3}$ | $4.4 \times 10^{-4}$ | $>10^{-3}$ | $>10^{-3}$ |

[Anti-complement activity]

(1) Anti-C1 (C1r̄, C1s̄) activity and inhibition of complement mediated hemolysis:

The anti-C1 esterase (C1r̄, C1s̄) activity was determined according to the method of Okamura et al. [K. Okamura, M. Muramatsu and S. Fujii, Biochem. Biophys. Acta, 295, 252–257 (1973)]. The inhibition of complement mediated hemolysis was determined according to the method of Baker et al. [B. R. Baker and E. H. Erickson, J. Med. Chem., 12, 408–414 (1969)]. The results obtained were as shown in Table 2. The figures in Table 2 have the following meanings:

C1r̄: Molar concentration of the test compound which inhibits 50% of the ability of C1r̄ to hydrolyse AAME (acetylarginin methyl ester) (ID$_{50}$).

C1s̄: Molar concentration of the test compound which inhibits 50% of the ability of C1s̄ to hydrolyse ATEE (acetyltyrosin ethyl ester).

The figure in parentheses shows the percent inhibition at a concentration of the compound of $1 \times 10^{-5}$ M.

Inhibition of complement mediated hemolysis (%): The inhibitory activity is shown in terms of percent inhibition of the compound at varied concentrations.

Compound No.: The compound number shown in Examples

TABLE 2

| Compound No. | Anti-C1 activity | | Inhibition of complement mediated hemolysis (%) | | | |
|---|---|---|---|---|---|---|
| | C1r̄ | C1s̄ | $1 \times 10^{-4}$ | $1 \times 10^{-5}$ | $1 \times 10^{-6}$ | $1 \times 10^{-7}$ |
| 1 | $4 \times 10^{-7}$ | $1 \times 10^{-7}$ | 100 | 100 | 91 | 27 |
| 3 | $1 \times 10^{-6}$ | $2 \times 10^{-6}$ | 97 | 60 | 8 | 11 |
| 4 | $4 \times 10^{-7}$ | $7 \times 10^{-8}$ | | 85 | 37 | 21 |
| 7 | $1 \times 10^{-7}$ | $2 \times 10^{-7}$ | 51 | 78 | 21 | 0 |
| 8 | $1 \times 10^{-5}$ | $4 \times 10^{-7}$ | 46 | 18 | 23 | NE |
| 10 | $2 \times 10^{-7}$ | $2 \times 10^{-7}$ | 97 | 75 | 9 | 2 |
| 11 | $1 \times 10^{-7}$ | $2 \times 10^{-7}$ | 96 | 56 | 6 | 13 |
| 12 | $3 \times 10^{-6}$ | $3 \times 10^{-6}$ | 87 | 55 | 27 | 3 |
| 13 | $3 \times 10^{-7}$ | $3 \times 10^{-7}$ | 94 | 42 | 5 | 4 |
| 14 | $7 \times 10^{-6}$ | $6 \times 10^{-6}$ | 61 | 15 | 1 | 3 |
| 15 | $2 \times 10^{-7}$ | $3 \times 10^{-7}$ | 98 | 89 | 23 | 2 |
| 16 | (39) | $4 \times 10^{-7}$ | 99 | 77 | 24 | 10 |
| 17 | $7 \times 10^{-7}$ | $5 \times 10^{-7}$ | 98 | 72 | 9 | 0 |
| 18 | $4 \times 10^{-6}$ | $4 \times 10^{-6}$ | 92 | 97 | 56 | 20 |
| 19 | $4 \times 10^{-6}$ | $8 \times 10^{-6}$ | 98 | 86 | 22 | 1 |
| 20 | $2 \times 10^{-7}$ | $2 \times 10^{-7}$ | 95 | 46 | 5 | 0 |
| 21 | $7 \times 10^{-7}$ | $5 \times 10^{-7}$ | 0 | 66 | 14 | 0 |
| 22 | $3 \times 10^{-7}$ | $2 \times 10^{-7}$ | 100 | 99 | 90 | 48 |
| 25 | $7 \times 10^{-7}$ | $4 \times 10^{-7}$ | 64 | 26 | 1 | 0 |
| 27 | $1 \times 10^{-7}$ | $5 \times 10^{-8}$ | 100 | 100 | 97 | 44 |
| 28 | $3 \times 10^{-6}$ | $3 \times 10^{-7}$ | 100 | 99 | 60 | 6 |
| 30 | $5 \times 10^{-7}$ | $3 \times 10^{-7}$ | 14 | 90 | 40 | 6 |
| 31 | $2 \times 10^{-6}$ | $3 \times 10^{-6}$ | 98 | 99 | 92 | 76 |
| 32 | $2 \times 10^{-6}$ | $3 \times 10^{-6}$ | 93 | 97 | 67 | 22 |
| 33 | $1 \times 10^{-6}$ | $3 \times 10^{-6}$ | 75 | 39 | 7 | 22 |
| 44 | $>10^{-5}$ | $>10^{-5}$ | 89 | 21 | 0 | 18 |
| 50 | | | 49 | 16 | 1 | 11 |
| 51 | (18) | (21) | 54 | 6 | 1 | 0 |
| 52 | $>10^{-5}$ | $>10^{-5}$ | 48 | 15 | 6 | 14 |
| 54 | $>10^{-5}$ | $>10^{-5}$ | 12 | 10 | 10 | 4 |
| 57 | $3 \times 10^{-5}$ | $3 \times 10^{-6}$ | | 80 | 24 | 23 |
| 60 | (21) | $3 \times 10^{-7}$ | 60 | 22 | 9 | 4 |
| 63 | (15) | $4 \times 10^{-7}$ | 73 | 37 | 26 | 42 |
| 64 | (14) | $3 \times 10^{-6}$ | | 39 | 17 | 19 |
| 66 | $6 \times 10^{-6}$ | $4 \times 10^{-6}$ | 60 | 6 | 1 | 1 |
| 68 | $>10^{-5}$ | $>10^{-5}$ | 91 | 4 | 0 | 0 |
| 70 | $>10^{-5}$ | $>10^{-5}$ | 26 | 1 | 0 | 2 |
| Leupeptin | $2 \times 10^{-4}$ | $2 \times 10^{-5}$ | 97 | 52 | 0 | 0 |

(2) Forssman shock:

The experiment was performed according to the method of I. G. Offerness et al. [Biochem. Pharmacol., 27 (14) 1873–1878 (1978)]. Male Hartlay guinea pig of about 300 g in body weight was used. Each guinea pig of the control group was administered intravenously with 0.5 ml (minimum dose to cause the shock) of hemolysin (commercial hemolysin, 5,000 U as assayed by the method of Ogata) and the time elapsed until death was observed. For the test group, each guinea pig was administered intravenously with the test compound 5 minutes before the administration of hemolysin and the time (second) elapsed until death was observed. The results obtained were as shown in Table 3. As compared with the control group, the administered group showed a significant extension of survival time.

TABLE 3

|  | Group administered with compound | | | | |
|---|---|---|---|---|---|
|  | Control | Compound No. 27 | | Control | Compound No. 22 | |
|  | group (sec.) | 0.5 mg/kg (sec.) | 1.0 mg/kg (sec.) | group (sec.) | 1.0 mg/kg (sec.) | 3.0 mg/kg (sec.) |
| 1 | 165 | 732 | 740 | 530 | 240 | 745 |
| 2 | 345 | 740 | 820 | 390 | 630 | 1410 |
| 3 | 466 | 723 | Survival | 245 | 250 | 600 |
| 4 | 809 | 724 | Survival | 425 | 570 | 885 |
| 5 | 325 | 590 | 670 | 445 | 440 | 455 |
| 6 | 680 | 410 | 1325 | 530 | 675 | 435 |
| Average | 465 | 653 | >889 | 428 | 468 | 755 |

Method of administration:

The present compound is most suitably administered orally, though can be administered by injection. It is used as a drug either alone or in combination with other drugs. It is administered generally in the form of medicinal composition, though can be administered as simple substance wihout any additive. Examples of medicinal compositions include tablets, powders, capsules, syrups and solutions. An oral composition may contain common additives such as binders, diluents, lubricants, disintegrators and excipients. Oral solutions may be in the form of aqueous or oily suspension, solution, emulsion, syrup or elixir, or in the form of dry syrup which, before use, is readjusted with water or other suitable solvents. The solutions may contain common additives such as suspending agents, flavoring agents, diluents, or emulsifies. For injection, may be used aqueous suspensions or oily suspensions.

Dosage:

The present compound may be administered to mammals (including man) orally at a dose of 10 to 200 mg per day or by intravenous injection at a dose of 1 to 20 mg per day. However, these doses are presented solely for the sake of example. A suitable dose for a patient should be determined depending upon the age and body weight of the patient and the features of illness.

Examples of pharmaceutical formulations are described below.

Examples of pharmaceutical formulations:

(1) Capsules.

| The present compound | 100.0 mg |
|---|---|
| Lactose | 59.0 |
| Crystalline cellulose | 33.4 |
| Calcium carboxymethylcellulose | 3.6 |
| Magnesium stearate | 4.0 |
| Total | 200.0 mg |

(2) Fine granules.

| The present compound | 50.0 mg |
|---|---|
| Lactose | 249.0 |
| Mannitol | 75.0 |
| Corn starch | 110.0 |
| Hydroxypropylcellulose | 16.0 |
| Total | 500.0 mg |

(3) Injections.

| The present compound | 5.0 mg |
|---|---|
| Water for injection | 2 ml |

Made up to injections in a customary manner.

Toxicity:

The median lethal dose (LD$_{50}$) of the present compound is as shown in Table 4.

TABLE 4

| Compound No. | LD$_{50}$ mg/kg | |
|---|---|---|
|  | IP | PO |
| 22 | 200 | 2,500 |
| 27 | 200 | 2,500 |

Examples of preparation of the present compounds are described below. The physical data of each compound are summarized in Table 5.

EXAMPLE 1 (COMPOUND NO. 1)

Synthesis of 6-amidino-2-naphthyl benzoate:

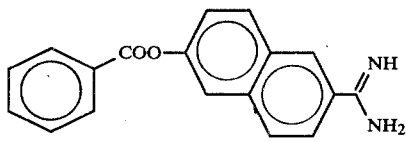

In 50 ml of pyridine, was suspended 2.8 g of 6-amino-2-naphthol methanesulfonate. To the resulting suspension, while being cooled in ice, was added with stirring 14.1 g of benzoyl chloride. The mixture was stirred for one hour while cooling in ice and then overnight at room temperature. After completion of the reaction, ethylether was added to the reaction mixture to form a precipitate which was collected by filtration. The precipitate was dissolved in methanol and the resulting solution was added to a saturated aqueous sodium hydrogencarbonate solution to form a precipitate. The precipitate was collected by filtration to obtain carbonate of 6-amidino-2-naphthyl benzoate. To the carbonate suspended in methanol, was added methanesulfonic acid followed by ethyl ether to obtain 2.4 g of a colorless powder of 6amindino-2-naphthyl benzoate methanesulfonate.

EXAMPLE 2 (COMPOUND NO. 2)

Synthesis of 6-amidino-2-naphthyl 2-methylbenzoate:

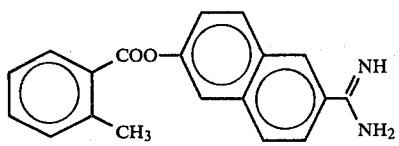

To 50 ml of anhydrous pyridine, was added 2.4 g of 2-methylbenzoic acid followed by 4.4 g of DCC under cooling in ice. After stirring for 30 minute and adding 5.0 g of 6amidino-2-naphthol methanesulfonate, the mixture was stirred overnight at room temperature. The precipitate was collected by filtration and washed with a small volume of pyridine, then successively with ethylether and acetone. The precipitate was dissolved in DMF and the insolubles were removed by filtration. Ethylether was added to the filtrate and the precipitated crystals were recrystallized from ethanol to obtain 1.4 g of flaky colorless crystals of 6amidino-2-napthyl 2-methyl benzoate methanesulfonate.

EXAMPLE 3 (COMPOUND NO. 3)

Synthesis of 6-amidino-2-naphthyl 3-methylbenzoate:

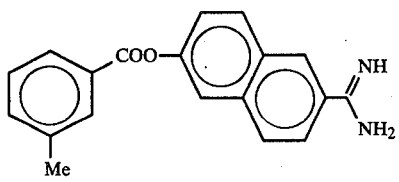

To a solution of 2.3 g of m-methylbenzoic acid in 30 ml of anhydrous pyridine, was added 4.4 g of DCC. To the stirred mixture, while being cooled in ice, was added 5 g of 6-amidino-2-naphthol methanesulfonate. After stirring for 24 hours, the insolubles were removed by filtration and ethylether was added to the filtrate. On separation of the resulting oily substance by decantation, it crystallized. The crystals were recrystallized from a methanol-ether mixture to obtain 2.2 g of 6-amino-2-naphthyl 3-methylbenzoate methanesulfonate.

EXAMPLE 4

The following compounds were obtained by the procedures similar to those of Examples 1 to 3

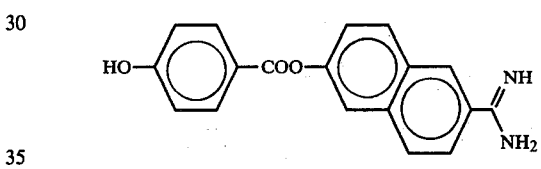

EXAMPLE 5 (COMPOUND NO. 11)

Synthesis of 6-amidino-2-naphthyl 4hydroxybenzoate:

To 50 ml of anhydrous DMF, were added 4.0 g of 6-amidino-2-naphthyl 4-benzyloxybenzoate methanesulfonate and 0.4 g of 10% Pd-C. The mixture was subjected to catalytic hydrogenation. After absorption of a stoichiometric amount of hydrogen, the reaction mixture was removed of Pd-C by filtration. After adding ethyl-ether to the stirred filtrate, the precipitate was collected by filtration and recrystallized from a DMF-ethylether mixture to obtain 2.4 g of a white powder of 6-amidino-2-naphthyl 4-hydroxybenzoate methanesulfonate.

EXAMPLE 6

The following compounds were obtained by the procedures similar to those of Examples 1 to 3.

-continued

| Compound No. | |
|---|---|
| 14 | 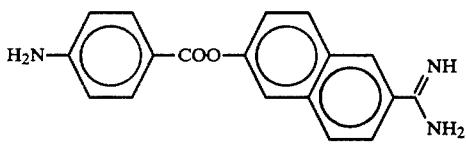 (row 14: CH3OOC–⌬–COO–naphthyl–C(=NH)NH2) |

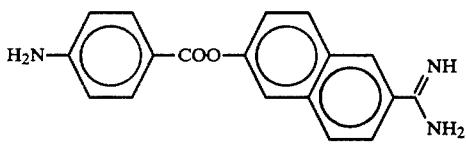

EXAMPLE 8 (COMPOUND NO. 21)

Synthesis of 6-amidino-2-naphthyl 4-benzyloxycarbonylaminomethylbenzoate:

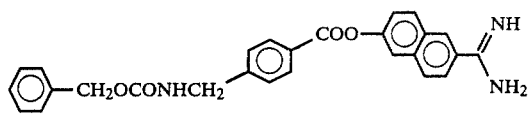

To 50 ml of dried pyridine, were added 5.1 g of 4-benzyloxycarbonylaminomethylbenzoic acid and 4.4 g of DCC. The mixture was stirred under cooling in ice for 30 minutes, admixed with 5.0 g of 6-amidino-2-naphthol methanesulfonate and stirred for one hour under cooling in ice, then overnight at room temperature. The reaction mixture was filtered* and the filtrate was mixed with ethyl ether. The precipitate which was formed was collected by filtration and recrystallized from a DMF-ethanol mixture to obtain 3.8 g of a white powder of a white powder of 6-amidino-2-naphthyl 4-benzyloxycarbonylaminomethylbenzoate methanesulfonate.

*The precipitate collected on the filter is dissolved in DMF by heating, and insolubles are filtered off, another 3.5 g of a white powder of the intended product is obtained from the filtrate by the addition of ethylether and subsequent filtration to collect the precipitate.

EXAMPLE 9 (COMPOUND NO. 22)

Synthesis of 6-amidino-2-naphthyl 4-aminomethylbenzoate:

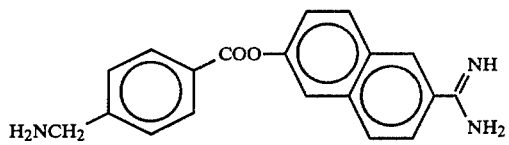

To a solvent mixture comprising 100 ml of methanol and 20 ml of DMF, were added 5.0 g 6-amidino-2-naphthyl 4-benzyloxycarbonylaminomethylbenzoate methanesulfonate, 1.0 g of 10% Pd-C and 1.1 g of methanesulfonic acid. Hydrogen was introduced into the mixture with vigorous stirring for 3 hours. After completion of the reaction, the reaction mixture was filtered and the filtrate was concentrated to about half the volume. Ethyl ether was added to the concentrate and the precipitated crystals were collected by filtration to obtain 3.0 g of a white powder of 6-amidino-2-naphthyl 4-aminomethylbenzoate dimethanesulfonate.

EXAMPLE 7 (COMPOUND NO. 20)

Synthesis of 6-amidino-2-naphthyl 4-aminobenzoate:

A mixture of 3.0 g of 6-amidino-2-naphthyl 4-nitrobenzoate methanesulfonate, 0.88 g of methanesulfonic acid, 0.3 g of 10% Pd-C and anhydrous DMF was subjected to catalytic hydrogenation. After absorption of a stoichiometric quantity of hydrogen, the reaction mixture was freed from Pd-C by filtration. After adding ethylether to the filtrate with stirring, the precipitate was collected by filtration and recrystallized from a DMF-ethylether mixture to obtain 3.5 g of a white powder of 6-amidino-2-naphthyl 4-aminobenzoate dimethanesulfonate.

EXAMPLE 10

The following compounds were prepared by the procedure similar to that of Example 8 or 9.

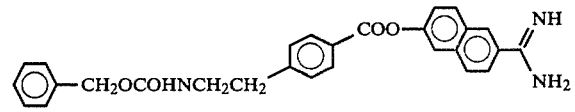

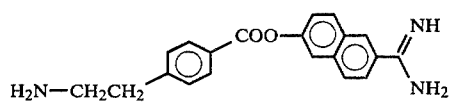

EXAMPLE 11 (COMPOUND NO. 23)

Syntheis of 6-amidino-2-naphthyl 3-dimethylaminobenzoate:

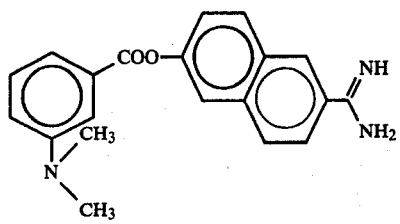

To 70 ml of dried pyridine, were added 2.9 g of 3-dimethylaminobenzoic acid and 4.4 g of DCC. The mixture was stirred for 30 minutes while cooling in ice. After addition of 5.0 g of 6-amidino-2-naphthol methanesulfonate, the mixture was further stirred for one hour under cooling in ice and then overnight at room temperature. The reaction mixture was filtered and the filtrate was mixed with ethyl ether. The precipitate which was formed was collected by filtration, dissolved in a small quantity of methanol, and added to a saturated aqueous sodium hydrogencarbonate solution while being stirred. The precipitated crystals were collected by filtration to obtain 3.8 g of 6amidino-2-naphthyl 3-dimethylaminiobenzoate carbonate having a melting point of about 120° C. (decomp.). The crystals were suspended in ethanol, mixed with 1.4 g of acetic acid and stirred to form a clear solution from which crystals were precipitated after some time. The crystals were collected by filtration and recrystallized from ethanol to obtain 2.5 g of a white powder of 6-amidino-2-naphthyl 3dimethylaminobenzoate acetate.

EXAMPLE 12 (COMPOUND NO. 24)

Synthesis of 6-amidino-2-naphthyl 4-dimethylaminobenzoate:

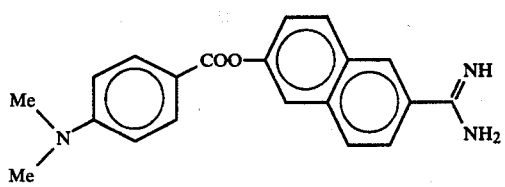

To 50 ml of dried pyridine, were added 2.9 g of 4-dimethylaminobenzoic acid and 4.4 g of DCC. The mixture was stirred for 30 minutes while being cooled in ice. After adding 5.0 g of 6-amidino-2-naphthol methanesulfonate, the mixture was further stirred for one hour under cooling in ice, then overnight at room temperature. The reaction mixture was filtered, the collected precipitate was washed with pyridine and ethyl ether and heated in DMF. The insolubles were filtered off and the filtrate was mixed with ethyl ether. The precipitate which was formed was collected by filtration and recrystallized from a mixture of methanol and ethyl ether to obtain 1.2 g of a white powder of 6-amidino-2-naphthyl 4-dimethylaminobenzoate methanesulfonate.

EXAMPLE 13 (COMPOUND NO. 25)

Synthesis of 6-amindino-2-naphthyl 4-acetylaminobenzoate:

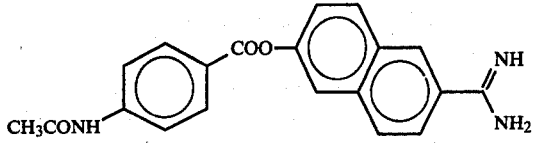

The synthesis was performed as in Example 2.

EXAMPLE 14 (COMPOUND NO. 26)

Synthesis of 6-amidino-2-naphthyl 3-guanidinobenzoate:

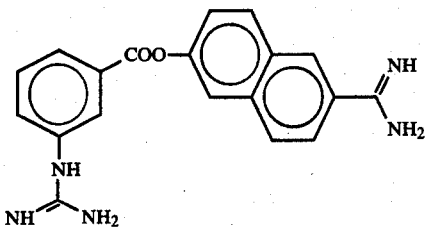

In 200 ml of ethanol, was suspended 32 g of m-aminobenzoic acid hydrochloride. After the addition of 15.5 g of cyanamide ($NCNH_2$), the mixture was stirred for 24 hours at an oil bath of a temperature of 55° C. The precipitate was collected by filtration, mixed with a saturated aqueous sodium hydrogencabonate solution and the precipitated crystals were collected by filtration. The crystals were suspended in ethanol, mixed with methanesulfonic acid, and the resulting solution was mixed with ethyl ether to yield an oily substance which was separated by decantation to obtain 27 g of m-guanidinobenzoic acid methanesulfonate.

To a solution of 4.7 g of m-guanidinobenzoic acid methanesulfonate in 50 ml of anhydrous pyridine, was added 4.4 g of DCC. To the mixture, while being cooled in ice and stirred, was added 5.0 of 6-amidino-2-naphthol methanesulfonate. After having been stirred for 24 hours, the reaction mixture was freed from the insolubles by filtration and the filtrate was mixed with ether. The oily substance which was formed was crystallized by adding ethyl acetate. Recrystallization from a mixture of methanol and ether gave 3.2 g of 6-amidino-2-naphthyl 3 -guanidinobenzoate dimethanesulfonate.

EXAMPLE 15 (COMPOUND NO. 27)

Synthesis of 6-amidino-2-naphthyl 4-quanidinobenzoate:

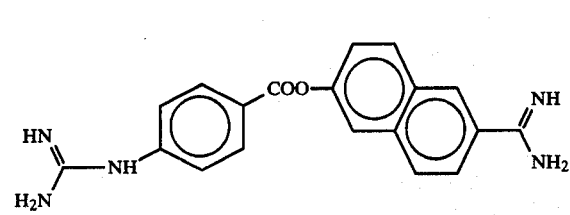

Method A

To 100 ml of thionyl chloride, was added 21.6 g of 4-guanidinobenzoic acid hydrochloride. The mixture was heated with stirring under reflux for one hour. n-Hexane was added to the reaction mixture to obtain pale yellow crystals of 4-guanidinobenzoyl chloride hydrochloride. Into 200 ml of pyridine, was dissolved 28.2 g of 6-amidino-2-naphthol methanesulfonate. To the resulting solution, while being cooled in ice, was added 4-guanidinobenzoyl chloride hydrochloride which was obtained above. The mixture was stirred under cooling in ice for one hour and then at room temperature overnight. After completion of the reaction, the reaction mixture was mixed with about 300 ml of ethyl ether. The oily substance which was separated was dissolved in about 300 ml of water and the insolubles were removed by filtration. A saturated aqueous sodium hydrogencarbonate solution was added to the filtrate to precipitate pale yellow crystals. The crystals were collected by filtration and washed with water and acetone to obtain 30 g (63.7% yield) of 6-amidino-2-naphthyl 4-guanidinobenzoate carbonate. The carbonate was suspended in 100 ml of methanol. Upon addition of 17 g of methanesulfonic acid to the suspension, a clear solution was formed accompanied by effervescence. About 200 ml of ethyl ether was added to the solution to precipitate white crystals which were collected by filtration to obtain 6-amidino-2-naphthyl 4-guanidinobenzoate dimethanesulfonate.

6-Amidino-2-naphthyl 4-guanidinobenzoate di-p-toluenesulfonate was obtained in a similar manner. 6-Amidino-2-naphthyl 4-guanidinobenzoate dihydrochloride was obtained by adding a DMF-HCl mixture to the carbonate obtained above.

Method B

To 100 ml of pyridine, were added 8.6 g of 4-guanidinobenzoic acid hydrochloride and 9.0 g of DCC. The mixture was stirred for one hour under cooling in ice (reaction mixture A). To 100 ml of pyridine, was added 113 g of 6amidino-2-naphthol methanesulfonate. To the mixture, while being cooled in ice and stirred, was added the reaction mixture A portionwise over a period of one hour. After completion of the addition, the resulting mixture was stirred for another hour under cooling in ice, then overnight at room temperature. The precipitated crystals were collected by filtration and washed with pyridine and acetone. The crystals were then dissolved in about 200 ml of water and the insoluble DCU was removed by filtration. A saturated aqueous sodium hydrogencarbonate solution was added to the filtrate to precipitate pale yellow crystals. The crystals were washed with water and acetone to obtain 15 g (79.8% yield) of 6-amidino-2-naphthyl 4-guanidinobenzoate carbonate. From this carbonate other acid addition salts may be obtained by the procedure described in method A.

EXAMPLE 16 (COMPOUND NO. 28)

Synthesis of 6-amidino-2-naphthyl 4-(Nα-methyl)-guanidinobenzoate:

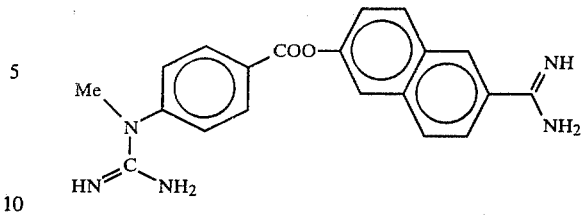

In 150 ml of methanol, was suspended 19 g of p-methylaminobenzoic acid hydrochloride. After adding 8.4 g of cyanamide, the mixture was stirred overnight at 50° C. The reaction mixture was freed from the solvent by distillation under reduced pressure and the residue was mixed with 20 ml of ethanol and thoroughly stirred. After further addition of 200 ml of ethyl acetate, the mixture was stirred continually to deposit a brown solid substance. The solid matter was collected by filtration and the treatment was repeated to obtain 14 g of a pale brown powder of 4-(Nα-methyl)guanidinobenzoic acid hydrochloride.

NMR (DMSO-d$_6$)δ: 3.33 (3H, S)

In 100 ml of pyridine, was dissolved 4.6 g of the above 4-(Nα-methyl)guanidinobenzoic acid hydrochloride followed by 6.2 g of DCC. The mixture was stirred at room temperature for 30 minutes, then admixed with 5.6 g of 6-amidino-2-naphthol methanesulfonate, and stirred overnight at room temperature. The insoluble substance was collected by filtration, suspended in 50 ml of water, and freed from the insolubles. To the mother liquor, was added 100 ml of a saturated sodium hydrogencarbonate solution. The mixture was stirred while being cooled in ice. The crystals which were precipitated were collected by filtration and suspended in 5 ml of methanol. After adding methanesulfonic acid with stirring, ethyl ether was added to precipitate the crystals. After removing the solvent, the residue was dissolved in hot methanol, then the solution was cooled, and mixed with ethyl ether to precipitate the crystals. The crystals were collected by filtration to obtain 0.8 g of a grayish white powder of 6-amidino-2-naphthyl 4-(Nα-methyl)guanidinobenzoate dimethanesulfonate.

EXAMPLE 17

The following compounds were prepared in a similar manner to that in Example 16.

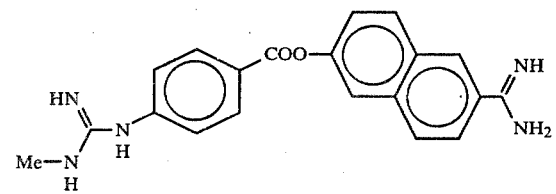

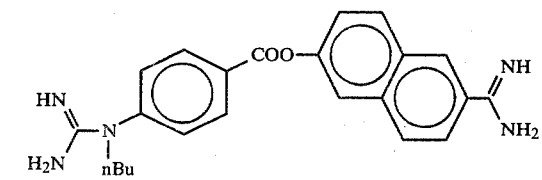

EXAMPLE 18

The following compounds were prepared as in Example 1 to 3.

| | Compound No. |
|---|---|
| ![structure] NH2SO2–C6H4–COO–naphthyl–C(=NH)NH2 | 29 |
| ![structure] CH3S–C6H4–COO–naphthyl–C(=NH)NH2 | 30 |
| ![structure] OHC–C6H4–COO–naphthyl–C(=NH)NH2 | 31 |
| ![structure] CH3CO–C6H4–COO–naphthyl–C(=NH)NH2 | 32 |
| ![structure] CF3–C6H4–COO–naphthyl–C(=NH)NH2 | 33 |
| ![structure] O2N–C6H3(CH3)–COO–naphthyl–C(=NH)NH2 | 34 |

EXAMPLE 19 (COMPOUND NO. 35)

Synthesis of 6-amidino-2-naphthyl 4-amino-3-methylbenzoate:

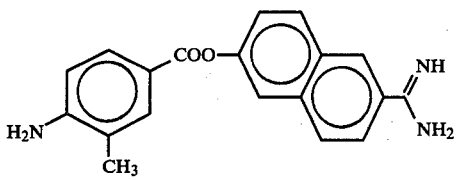

To 25 ml of DMF (anhydrous), were added 2.2 g of 6-amidino-2-naphthyl 3-methyl-4-nitrobenzoate methanesulfonate, 0.63 g of methanesulfonic acid, and 0.23 g of 10% Pd-C. Into the mixture, while being vigorously stirred, was introduced hydrogen. After removal of Pd-C by filtration, the reaction mixture was mixed with ethyl ether to separate an oily substance which was washed with ether and recrystallized from an ethanol-ethyl ether mixture to obtain 2.8 g of a white to pale brown powder of 6-amidino-2-naphthyl 4-amino-3-methylbenzoate dimethanesulfonate.

EXAMPLE 20-1

Synthesis of 4-guanidino-3-methylbenzoic acid hydrochloride:

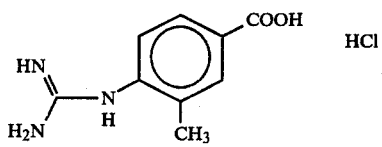

To 140 ml of ethanol, was added 22.6 g of 4-amino-3-methylbenzoic acid hydrochloride followed by 7.6 g of cyanamide. After having been stirred overnight at 60° C., the reaction mixture was freed from the solvent by distillation under reduced pressure and mixed with acetone to collect the crystals by filtration. The crystals were washed with acetone and recrystallized from a mixture of ethanol and ethyl acetate to obtain 8.9 g of white granular crystals of 4-guanidino-3-methylbenzoic acid hydrochloride.

mP: ≈231° C. (decomp.)

IR$\nu_{Max}^{KBr}$ cm$^{-1}$: 3350, 3100, 1690, 1660, 1595

NMR (DMSO-d$_6$) δ:2.32 (3H, S), 7.22–8.00 (8H, m), 9.50–11.00 (1H, br)

EXAMPLE 20-2 (COMPOUND NO. 36)

Synthesis of 6-amidino-2-naphthyl 4-guanidino-3-methylbenzoate:

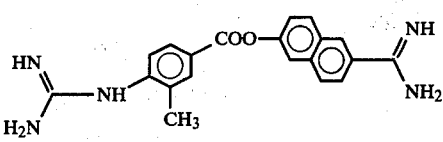

To 50 ml of anhydrous pyridine, was added 4.1 g of 4-guanidino-3-methylbenzoic acid hydrochloride. After addition of 4.4 g of DCC under cooling in ice, the mixture was stirred for 30 minutes and admixed with 5.0 g of 6-amidino-2-naphthol methanesulfonate. The mixture was stirred overnight at room temperature, then mixed with ethyl ether, and the crystals were collected by filtration. The crystals were washed with ethyl ether, dissolved in water, and the insolubles were removed by filtration. The filtrate was added to a stirred saturated aqueous sodium hydrogencarbonate solution. The precipitated crystals were collected by filtration, washed with water and acetone, and dried to obtain the carbonate of intended compound. The carbonate was added to methanol and mixed with 2.5 equivalents of methanesulfonic acid while cooling in ice. After addition of ethyl ether, the separated oily substance was crystallized from ethanol to obtain 4.8 g of white granular crystals of 6-amidino-2-naphthyl 4-guanidino-3-methylbenzoate dimethanesulfonate.

EXAMPLE 21 (COMPOUND NO. 37)

Synthesis of 6-amidino-2-naphthyl 2-chloro-4-nitrobenzoate:

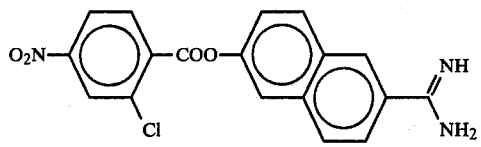

The synthesis was performed as in Examples 1 to 3.

EXAMPLE 22 (COMPOUND NO. 38)

Synthesis of 6-amidino-2-naphthyl 2-chloro-4-aminobenzoate:

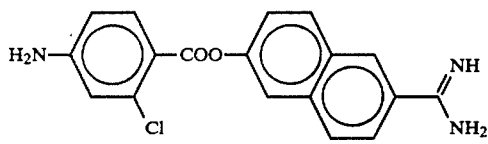

The synthesis was performed as in Example 7 or 19.

EXAMPLE 23-1

Synthesis of 2-chloro-4-guanidinobenzoic acid.

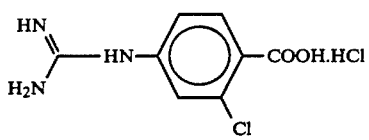

The synthesis was performed as in Example 20-1. mP 136°–140° C.
IR$\nu_{max}^{KBr}$cm$^{-1}$: 3330, 3150, 1710 (shoulder), 1660, 1595, 1220, 1205, 1190, 780, 560, 530, 520
NMR (DMSO-d$_6$)δ: 2.55 (3H, S), 7.17–7.55 (2H, m), 7.67–8.17 (4H, m), 8.58 (2H, S). 10.25 (1H, S)

EXAMPLE 23-2 (COMPOUND NO. 39)

Synthesis of 6-amidino-2-naphthyl 2-chloro-4-guanidinobenzoate:

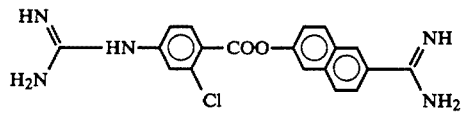

The synthesis was performed as in Example 20-2.

EXAMPLE 24 (COMPOUND NO. 40)

Synthesis of 6-amidino-2-naphtyl phenylacetate:

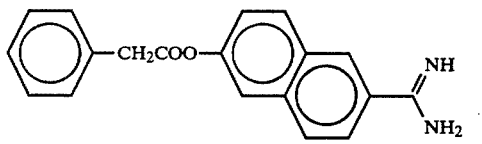

To a solution of 2.4 g of phenylacetic acid in 50 ml of anhydrous pyridine, while being cooled and stirred, was added 4.4 g of DCC. After 30 minutes, to the mixture was added 5.0 g of 6-amidino-2-naphthol methanesulfonate. The mixture was stirred at room temperature for 24 hours, mixed with ethyl ether, and the precipitate was collected by filtration. The precipitate was dissolved in DMF and the insolubles were filtered off. The filtrate containing the DMF-soluble substances was mixed with ethyl ether, the resulting precipitate was collected by filtration and recrystallized from a mixture of DMF and ethyl ether to obtain 3.0 g of a white powder of 6-amidino-2-naphthyl phenylacetate methanesulfonate.

EXAMPLE 25 (COMPOUND NO. 41)

Synthesis of 6-amidino-2-naphthyl α-methylphenylacetate:

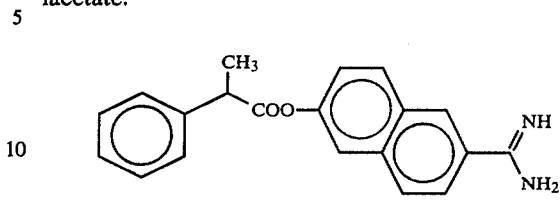

To 50 ml of dried pyridine, were added 3.0 g of α-methylphenylacetic acid and 4.9 g of DCC. The mixture was stirred for 30 minutes under cooling in ice. After adding 5.6 g of 6-amidino-2-naphthol methanesulfonate, while being cooled in ice, the mixture was stirred for one hour, then overnight. The reaction mixture was filtered to collect the precipitate. The precipitate was washed with pyridine and ethyl ether, added to DMF and heated. The insolubles were filtered off and ethyl ether was added to the filtrate to collect the precipitate by filtration. The precipitate was recrystallized from a mixed solvent comprising ethanol and ethyl ether to obtain 1.8 g of a white powder of 6-amidino-2-naphthyl α-methylphenylacetate methanesulfonate.

EXAMPLE 26

The following compounds were obtained as in Examples 1 to 3 or Examples 24 and 25

| | Compound No. |
|---|---|
| ![structure] | 42 |
| ![structure] | 43 |
| ![structure] | 44 |
| ![structure] | 45 |
| ![structure] | 46 |

-continued

| | Compound No. |
|---|---|
| O₂N—⟨⟩—CH₂—COO—[naphthyl]—C(=NH)NH₂ | |
| H₂N—⟨⟩—CH₂—COO—[naphthyl]—C(=NH)NH₂ | |
| H₃C—⟨⟩—CH₂—COO—[naphthyl]—C(=NH)NH₂ | |
| [3-CH₃-phenyl]—CH₂—COO—[naphthyl]—C(=NH)NH₂ | |
| MeO—⟨⟩—CH₂—COO—[naphthyl]—C(=NH)NH₂ | |
| [2-OMe-phenyl]—CH₂—COO—[naphthyl]—C(=NH)NH₂ | |

EXAMPLE 27 (COMPOUND NO. 47)

Synthesis of 6-amidino-2-naphthyl 3-phenylpropionate:

[Structure: Ph—CH₂CH₂—COO—(naphthyl)—C(=NH)NH₂]

In 30 ml of DMF, was suspended 1.2 g of 6-amidino-2-naphthyl cinnamate methanesulfonate. After addition of 0.4 g of 10% Pd-C, the mixture was subjected to catalytic hydrogenation. The reaction mixture was filtered and the filtrate was mixed with ethyl ether. The resulting precipitate was collected by filtration and recrystallized from a methanol-ethyl ether mixture to obtain 0.91 g of 6-amidino-2-naphthyl 3-phenylpropionate methanesulfonate.

EXAMPLE 28

The following compounds were obtained by the procedure similar to that of Example 27.

| | Compound No. |
|---|---|
| Me—⟨⟩—CH₂CH₂—COO—[naphthyl]—C(=NH)NH₂ | 48 |

-continued

| | Compound No. |
|---|---|
| MeO—[3,4-diMeO-phenyl]—CH₂CH₂—COO—[naphthyl]—C(=NH)NH₂ | 49 |
| CH₃COO—⟨⟩—CH₂CH₂—COO—[naphthyl]—C(=NH)NH₂ | 50 |

EXAMPLE 29 (COMPOUND NO. 51)

Synthesis of 6-amidino-2-naphthyl 4-aminophenylpropionate:

[Structure: H₂N—⟨⟩—CH₂CH₂—COO—(naphthyl)—C(=NH)NH₂]

The synthesis was carried out by a procedure similar to that in Example 27 using 6-amidino-2naphthyl 4-nitrocinnamate p-toluenesulfonate as starting material.

EXAMPLE 30

The following compounds were synthesized by the procedure similar to that of Example 27.

| | Compound No. |
|---|---|
| HN=C(NH₂)—NH—⟨⟩—CH₂—COO—[naphthyl]—C(=NH)NH₂ | 52 |
| HN=C(NH₂)—NH—⟨⟩—CH(CH₂CH₃)—COO—[naphthyl]—C(=NH)NH₂ | 53 |
| H₂N—⟨⟩—CH(CH₃)—COO—[naphthyl]—C(=NH)NH₂ | |
| [2-CH₃-phenyl]—CH₂CH₂—COO—[naphthyl]—C(=NH)NH₂ | |
| MeO—⟨⟩—CH₂CH₂—COO—[naphthyl]—C(=NH)NH₂ | |
| OHC—⟨⟩—CH₂CH₂—COO—[naphthyl]—C(=NH)NH₂ | |

EXAMPLE 31 (COMPOUND NO. 54)

Synthesis of 6-amidino-2-naphthyl 4-phenylbutyrate:

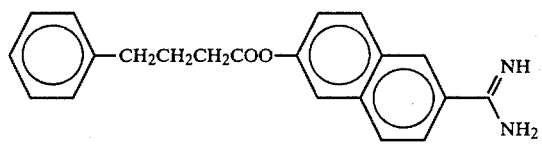

To a solution of 2.9 g of 4-phenylbutyric acid in 50 ml of anhydrous pyridine, while being cooled in ice and stirred, was added 4.4 g of DCC. After 30 minutes, 5.0 g of 6-amidino-2-naphthol methanesulfonate was added and the mixture was stirred for 24 hours at room temperature and removed of insolubles. Ethyl ether was added to the filtrate and the precipitate was collected by filtration. The precipitate was recrystallized from a DMF-ethyl ether mixture to obtain 2.3 g of a white powder of 6-amidino-2-naphthyl 4-phenylbutyrate methanesulfonate.

EXAMPLE 32

The following compounds were obtained by the procedure similar to that in Example 7 or 31.

EXAMPLE 33 (COMPOUND NO. 57)

Synthesis of 6-amidino-2-naphthyl cinnamate:

To a solution of 9.9 g of 6-amidino-2-naphthol methanesulfonate in 100 ml of anhydrous pyridine, while being cooled in ice and stirred, was added 5.8 g of cinnamoyl chloride. After having been stirred overnight at room temperature, the mixture was admixed with ethyl acetate and the resulting precipitate was collected by filtration. The precipitate was suspended in methanol, mixed with a saturated aqueous sodium hydrogencarbonate solution with stirring, and the precipitate was collected by filtration. After having been washed with water and acetone, the precipitate was suspended in methanol and mixed with methanesulfonic acid. After having been stirred for same time, the mixture was admixed with ethyl ether, the precipitate was collected by filtration and recrystallized from a methanol-ethyl ether mixture to obtain 7.1 g of 6-amidino-2-naphthyl cinnamate methanesulfonate.

EXAMPLE 34

The following compounds were obtained by the procedure similar to that of Example 1, 2, 3 or 33.

EXAMPLE 35 (COMPOUND NO. 63)

Synthesis of 6-amidino-2-naphthyl 4-aminocinnamate:

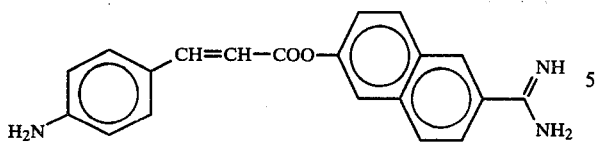
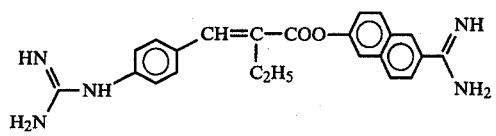

In 60 ml of acetic acid, was suspended 3 g of 6-amidino-2-naphthyl 4-nitrocinnamate tosylsulfonate. To the suspension, while being cooled in ice and stirred, was added 1.8 g of zinc dust. The mixture was stirred for 24 hours and removed of insolubles by filtration. The filtrate was neutralized, admixed with a saturated aqueous sodium hydrogencarbonate solution and the precipitate was suspended in methanol and admixed with methanesulfonic acid to dissolve the precipitate. Ethyl ether was added to the solution and the resulting oily substance was left standing at room temperature to solidify. Upon recrystallization from a methano-ethyl ether mixture, there was obtained 0.14 g of 6-amidino-2-naphthyl 4-aminocinnamate dimethanesulfonate.

EXAMPLE 36 (COMPOUND NO. 64)

Synthesis of 6-amidino-2-naphthyl 4-guanidinocinnamate:

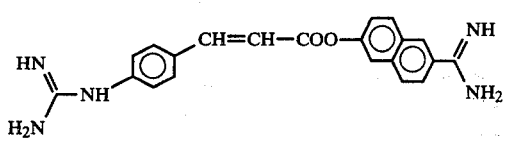

In 200 ml of ethanol, was suspended 23.4 g of p-aminocinnamic acid hydrochloride. After addition of 9.8 g of cyanamide, the mixture was stirred for 24 hours in an oil bath at a bath temperature of 50° C. The resulting solution was concentrated under reduced pressure and slowly added to a saturated aqueous sodium hydrogencarbonate solution. The precipitate was collected by filtration, washed successively with water and acetone, and suspended in methanol. The precipitate was dissolved by addition of methanesulfonic acid and the insolubles were removed by filtration. Ethyl ether was added to the filtrate and an oily substance which was formed was left standing at room temperature to crystallize. Upon recrystallization from a methanol-ethyl ether mixture, there was obtained 4.8 g of 4-guanidinocinnamic acid dimethanesulfonate.

To a solution of 3.0 g of 4-guanidinocinnamic acid methanesulfonate in 30 ml of anhydrous pyridine, was added 2.4 g of DCC. To the mixture, while being cooled in ice and stirred, was added 2.8 g of 6-amidino-2-naphthol methanesulfonate. After having been stirred for 24 hours, the reaction mixture was filtered to remove insolubles and the filtrate was mixed with ethyl ether to separate an only substance which was left standing at room temperature to crystallize. Upon recrystallization from a methanol-ethyl ether mixture, there was obtained 2.4 g of 6-amidino-2-naphthyl 4-guanidinocinnamate dimethanesulfonate.

EXAMPLE 37 (COMPOUND NO. 65)

Synthesis of 6-amidino-2-naphthyl 4-guanidino-α-ethylcinnamate:

The synthesis was performed as in Example 36.

EXAMPLE 38

The following compounds were synthesized by the procedure similar to that in Example 1, 2, 3 or 33.

| | Compound No. |
|---|---|
| (3-CF₃-phenyl)-CH=CH-COO-naphthyl-amidine | 66 |
| (2-CH₃-phenyl)-CH=CH-COO-naphthyl-amidine | |
| (3-CH₃-phenyl)-CH=CH-COO-naphthyl-amidine | |
| (4-O₂N-phenyl)-CH=C(CH₃)-COO-naphthyl-amidine | |
| (4-OHC-phenyl)-CH=CH-COO-naphthyl-amidine | |
| (4-Me₂N-phenyl)-CH=CH-COO-naphthyl-amidine | |
| (4-CH₃CONH-phenyl)-CH=CH-COO-naphthyl-amidine | |
| (methylenedioxyphenyl)-CH=CH-COO-naphthyl-amidine | |

EXAMPLE 39 (COMPOUND NO. 67)

Synthesis of 6-amidino-2-naphthyl phenoxyacetate:

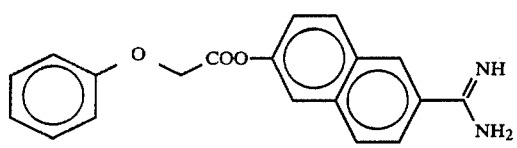

To a solution of 1.1 g of phenoxyacetic acid in 50 ml of pyridine, was added 2.2 g of DCC. The mixture was stirred at room temperature for 30 minutes, then admixed with 2.0 g of 6-amidino-2-naphthol methanesulfonate, and again stirred overnight at room temperature. The insolubles were removed by filtration, 500 ml of ethyl ether was added to the mother liquor and thoroughly stirred to precipitate a solid substance which was collected by filtration and recrystallized three times from methanol to obtain 0.3 g of 6-amidino-2-naphthyl phenoxyacetate methanesulfonate.

EXAMPLE 40

The following compounds were obtained by the procedure similar to that in Example 1, 2, 3, 7 or 39.

| | Compound No. |
|---|---|
| 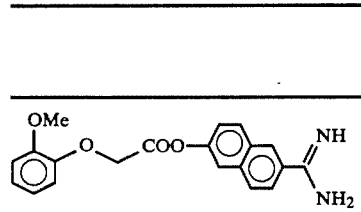 | 68 |
| 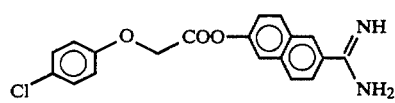 | 69 |
| 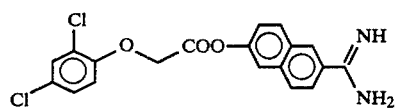 | 70 |
| 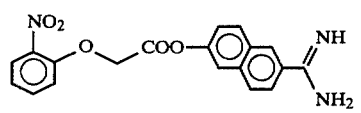 | 71 |
| 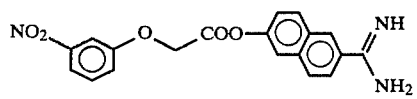 | 72 |
| 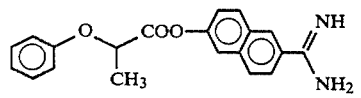 | |
| 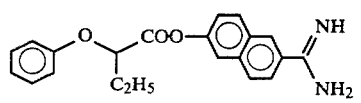 | |

| | Compound No. |
|---|---|
| 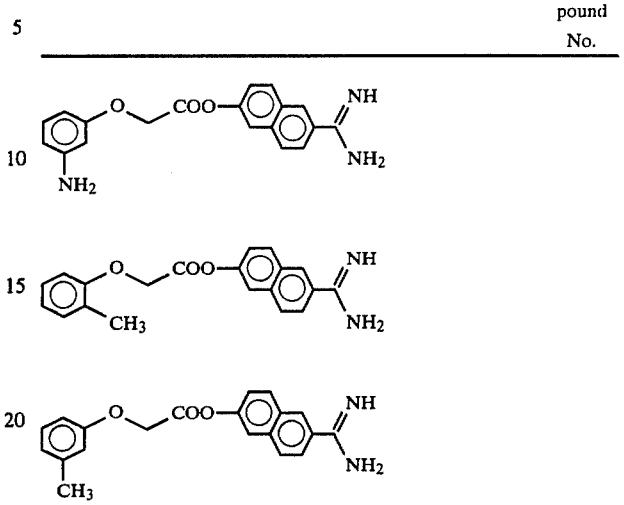 | |
| 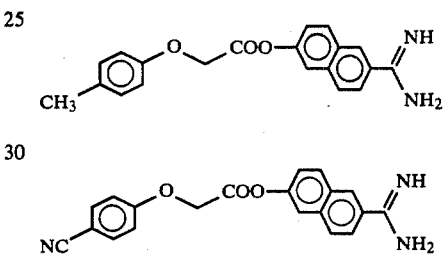 | |

EXAMPLE 41

The following compounds were obtained as in Example 1, 2 or 3

| | Compound No. |
|---|---|
| 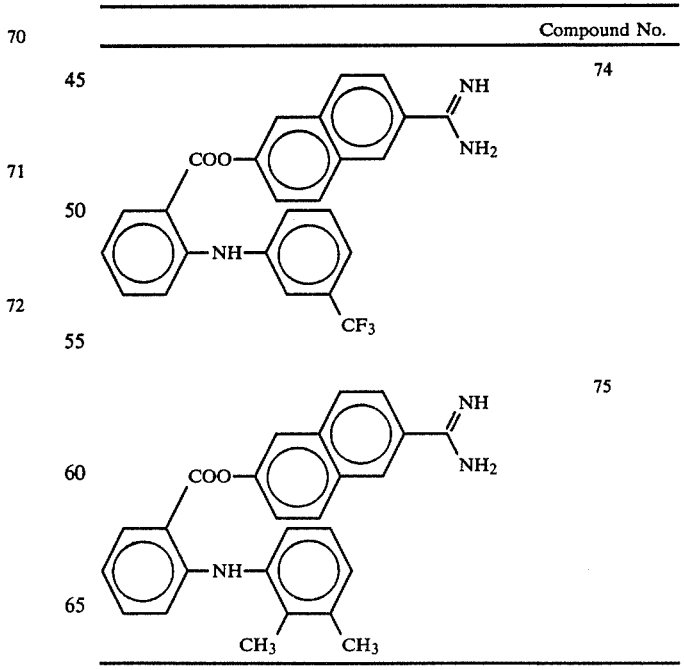 | 74<br>75 |

TABLE 5

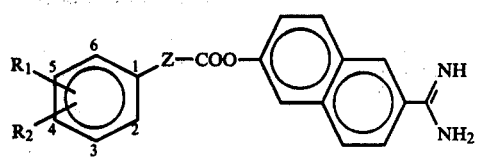

| Compound No. | R₁ | R₂ | Z | Salt | M.p. (°C.) | IR $\nu_{max}^{KBr}$ cm$^{-1}$ | NMR (DMSO—d₆) δ |
|---|---|---|---|---|---|---|---|
| 1 | H | H | — | MSA[1] | 252–255 | 3320, 3130, 1730, 1670, 1208 | 2.60 (3H, S[2]), 7.60–8.73 (11H, m[3]), 9.10–9.77 (4H, b[4]) |
| 2 | 2-CH₃ | H | — | MSA | 219–220 | 3300, 3130, 1730, 1675 | 2.48 (3H, S), 2.63 (3H, S), 7.25–8.40 (10H, m), 9.17–9.77 (4H, b) |
| 3 | 3-CH₃ | H | — | MSA | 168–172 | 3300, 3050, 1725, 1670, 1280, 1210 | 2.47 (3H, S), 2.50 (3H, S), 7.50–8.60 (10H, m), 9.16–9.76 (4H, b) |
| 4 | 4-CH₃ | H | — | MSA | 255–257 | 3300, 3120, 1730, 1680 | |
| 5 | 4-C(CH₃)₃ | H | — | MSA | 286–288 | 3300, 3100, 1730, 1670, 1265, 1200, 1180, 1045, 695, 540 | 1.33 (9H, S), 2.50 (3H, S), 7.43–8.80 (10H, m), 9.15–9.83 (4H, b) |
| 6 | 3-CH₃ | 4-CH₃ | — | MSA | 219–222 (dec.) | 3350, 3100, 1730, 1670 | 2.38 (6H, S), 2.50 (3H, S), 7.33–8.85 (9H, m), 9.22–9.82 (4H, b) |
| 7 | 4-OCH₃ | H | — | MSA | 263–265 | 3350, 3100, 1715, 1675, 1600, 1260, 1210, 1170, 1150, 690, 550, 525 | 2.47 (3H, S), 3.90 (3H, S), 7.57–8.87 (10H, m), 8.90–10.02 (4H, b) |
| 8 | 4-OCH₂CH₂CH₂CH₃ | H | — | MSA | 231–233 | 3320, 3130, 1720, 1680 | |
| 9 | 4-OCH₂—C₆H₅ | H | — | MSA | 268–269 | 3300, 3100, 1720, 1665, 1600, 1275, 1250, 1195, 1165, 760, 695, 550, 530, 520 | 3.10 (3H, S), 5.37 (2H, S), 6.77–8.53 (19H, m) |
| 10 | 3,4-methylene-dioxy | | — | MSA | 263–267 | 3350, 3150, 1720, 1670, 1500, 1285, 1265, 1205, 1145, 755, 550, 525 | 2.47 (3H, S), 6.20 (2H, S), 6.97–8.82 (9H, m), 9.07–9.77 (4H, b) |
| 11 | 4-OH | H | — | MSA | 238–241 (dec.) | 3450–2850, 1730, 1670, 1600, 1585, 1140, 1050, 1040, 715, 690, 550 | 2.57 (3H, S), 7.50–8.85 (10H, m), 8.98–9.82 (4H, b), 10.65 (1H, S) |
| 12 | 2-OCOCH₃ | H | — | MSA | | 3400–3000, 1730, 1675, 1205, 1190, 1040, 550, 530 | 2.47 (6H, S), 6.70–8.80 (10H, m), 9.32–10.22 (4H, b) |
| 13 | 4-OCOCH₃ | H | — | MSA | 246–249 (dec.) | 3350, 3100, 1750, 1730, 1670, 1270, 1240, 1190, 690, 545, 530 | 2.38 (3H, S), 2.57 (3H, S), 7.30–8.92 (10H, m), 8.98–10.28 (4H, b) |
| 14 | 4-COOCH₃ | H | — | MSA | 258–260 | 3350, 3050, 1730 (sh[5]), 1720, 1205, 1190, 715, 555, 530 | 2.52 (3H, S), 3.95 (3H, S), 7.52–8.78 (10H, n), 9.22–9.87 (4H, b) |
| 15 | 4-F | H | — | MSA | 243–245 | 3400–3000, 1730, 1650, 1600, 1265, 1240, 1205, 1145, 755, 550, 530 | 2.57 (3H, S), 7.23–8.93 (10H, m), 9.17–9.87 (4H, b) |
| 16 | 4-Cl | H | — | MSA | 215–217 (dec.) | 3320, 3100, 1725, 1675 | 2.57 (3H, S), 7.53–8.88 (10H, m), 9.22–9.92 (4H, b) |
| 17 | 4-Br | H | — | MSA | 255–259 | 3300, 3100, 1725, 1680, 1275, 1200, 1170, 1070, 1035, 740, 545, 515 | 2.53 (3H, S), 7.23–8.82 (10H, m), 9.22–9.83 (4H, b) |
| 18 | 4-NO₂ | H | — | MSA | 160–162 | 3300, 3050, 1740, 1670, 1520, 1260, 1240, 1210, 710, 540 | 3.13 (3H, S), 7.45–9.10 (15H, m) (TFA[6]). |
| 19 | 4-CN | H | — | MSA | 258–260 | 3400–3000, 2230, 1735, 1670, 1265, 1205, 760, 545, | 2.50 (3H, S) 7.52–8.78 (10H, m), 9.07–9.70 (4H, b) |

TABLE 5-continued

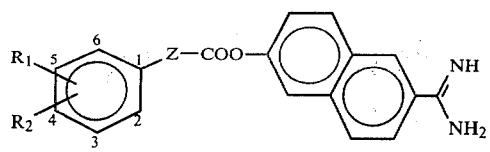

| Compound No. | R₁ | R₂ | Z | Salt | M.p. (°C.) | IR $\nu_{max}^{KBr}$ cm⁻¹ | NMR (DMSO—d₆) δ |
|---|---|---|---|---|---|---|---|
| 20 | 4-NH₂ | H | — | 2MSA | 136–139 (dec.) | 3500–2750, 1735, 1670, 1205, 1190, 1145, 1040, 780, 560, 535, 530 | 2.57 (6H, S), 6.77–8.83 (13H, m), 9.15–9.67 (4H, b) |
| 21 | 4-CH₂NHCOOCH₂—C₆H₅ | H | — | MSA | 160–165 | 3300, 3110, 1730, 1680 | 2.55 (3H, S), 4.20–4.50 (2H, b), 5.15 (2H, S), 7.17–8.60 (15H, m), 9.00–9.60 (4H, b) |
| 22 | 4-CH₂NH₂ | H | — | 2MSA | 242–244 | 3400–2750, 1725, 1665, 1190 | 2.53 (6H, S), 4.27 (2H, s), 7.53–8.77 (13H, m), 9.13–9.77 (4H, b) |
| 23 | 3-N(CH₃)₂ | H | — | H₂CO₃ | 120– (dec.) | | |
|  | 3-N(CH₃)₂ | H | — | CH₃COOH | 170–178 | 3400–2510, 1725, 1240 | 1.87 (3H, S), 3.02 (6H, S), 7.00–9.40 (m) |
| 24 | 4-N(CH₃)₂ | H | — | MSA | 223–229 | 3320, 3120, 1705, 1660, 1183 | 2.47 (3H, S), 3.01 (6H, S), 6.73–8.63 (10H, m), 9.00–9.60 (4H, b) |
| 25 | 4-NHCOCH₃ | H | — | MSA | 270–279 | 3600–2900, 1720, 1663, 1201 | |
| 26 | 3-NH—C(=NH)NH₂ | H | — | 2MSA | 43–46 | 3300, 3100, 1730, 1670, 1200 | 2.6 (6H, S), 7.50–8.70 (14H, m), 9.20–9.83 (4H, b), 10.23 (1H, S) |
| 27 | 4-NH—C(=NH)NH₂ | H | — | 2MSA | 217–220 | 3350, 3150, 1730, 1675 | |
|  | 4-NH—C(=NH)NH₂ | H | — | 2 CH₃—C₆H₄—SO₃H | 243–245 | 3320, 3110, 1722, 1676, 1250, 1200 | 2.30 (6H, S), 6.70–8.73 (22H, m), 8.97–9.73 (4H, b), 10.58 (1H, S) |
|  | 4-NH—C(=NH)NH₂ | H | — | 2HCl | 264–266 | 3400–2900, 1720, 1700, 1650 | 7.5 (d⁽⁷⁾), 7.7–8.8 (m), 9.6 (b), 9.8 (b), 10.9 (b) |
| 28 | 4-N(CH₃)—C(=NH)NH₂ | H | — | 2MSA | 243–245 | 3150, 1730, 1660 | 2.48 (6H, S), 3.42 (3H, S), 7.17–8.67 (14H, m), 9.10–9.67 (4H, m) |
| 29 | 4-SO₂NH₂ | H | — | MSA | 240–242 | 3400, 3340, 3100, 1729, 1680, 1205 | 2.20 (3H, S), 7.77–8.68 (10H, m), 10.03–10.53 (4H, b) |
| 30 | 4-SCH₃ | H | — | MSA | 260–263 | 3330, 3100, 1725, 1668 | 2.50 (3H, S), 2.57 (3H, S), 7.37–8.60 (10H, m), |

TABLE 5-continued

[Structure: R1 at position 5, R2 at position 4 on benzene ring (positions 1-6), with Z-COO- linked to naphthalene bearing C(=NH)NH2 group]

| Compound No. | R1 | R2 | Z | Salt | M.p. (°C.) | IR $\nu_{max}^{KBr}$ cm$^{-1}$ | NMR (DMSO—d$_6$) δ |
|---|---|---|---|---|---|---|---|
| 31 | 4-CHO | H | — | MSA | 182–185 | 3350, 3150, 1720, 1670, 1200 | 9.10–9.70 (4H, b) 2.47 (3H, S), 7.63–8.70 (10H, m), 9.26–9.89 (4H, b), 10.23 (1H, S) |
| 32 | 4-COCH$_3$ | H | — | MSA | 213–217 | 3300, 3100, 1730 1670, 1195 | 2.50 (3H, S), 2.67 (3H, S), 7.50–8.70 (10H, m), 9.17–9.67 (4H, b) |
| 33 | 3-CF$_3$ | H | — | MSA | 172–175 | 3320, 3150, 1733 1685, 1230 | |
| 34 | 4-NO$_2$ | 3-CH$_3$ | — | MSA | 235–238 (dec.) | 3330, 3120, 1730 1680, 1520, 1350 | 2.48 (3H, S), 2.62 (3H, S), 7.62–8.78 (9H, m), 9.18–9.75 (4H, b) |
| 35 | 4-NH$_2$ | 3-CH$_3$ | — | 2MSA | −117 (dec.) | 3300, 3100, 1725 1670 | 2.28 (3H, S), 2.57 (6H, S), 7.55–8.85 (12H, m), 9.22–9.85 (4H, b) |
| 36 | 4-NH—C(=NH)NH$_2$ | 3-CH$_3$ | — | 2MSA | −175 (dec.) | 3300, 3150, 1720 1600 | 2.40 (3H, S), 2.48 (6H, S), 7.37–8.70 (13H, m), 9.20–9.63 (4H, b), 9.78 (1H, b) |
| 37 | 4-NO$_2$ | 2-Cl | — | MSA | 239–242 (dec.) | 3400–3000, 1730 1670, 1520, 1210 | 2.50 (3H, S), 7.57–8.83 (9H, m), 9.13–9.80 (4H, b) |
| 38 | 4-NH$_2$ | 2-Cl | — | 2MSA | 126–128 | 3550–2800, 1730 1660, 1200, 1140, 1090, 1035, 775, 550 | |
| 39 | 4-NH—C(=NH)NH$_2$ | 2-Cl | — | 2MSA | 200–210 | 3450–2950, 1730 (Sh), 1670, 1200, 1040, 775, 550, 530 | 2.57 (3H, S), 7.50–8.82 (13H, m), 9.15–9.82 (4H, b), 10.45 (1H, S) |
| 40 | H | H | —CH$_2$— | MSA | 179–181 | 3350–3050, 1750 1660, 1215, 1135 710, 550, 530 | 2.50 (3H, S), 4.07 (2H, S), 7.20–8.83 (12H, m), 9.10–9.78 (4H, b) |
| 41 | H | H | —CH(CH$_3$)— | MSA | 167–169 | 3450–2900, 1750 1670, 1202 | |
| 42 | 4-CH$_2$CH(CH$_3$)CH$_3$ | H | —CH(CH$_3$)— | MSA | 195–197 | 3400–2750, 1748, 1670, 1200 | |
| 43 | 3-OCH$_3$ | H | —CH$_2$— | MSA | 161–162 | 3330, 3100, 1760, 1670 | 2.47 (3H, S), 3.78 (3H, S), 4.05 (2H, S), 6.73–8.67 (10H, m), 9.13–9.67 (4H, b) |
| 44 | 4-Cl | H | —CH$_2$— | MSA | 214–218 | 3300, 3100, 1740 1670, 1340 | 2.50 (3H, S), 4.10 (2H, S), 7.50–8.60 (10H, m), 9.17–9.70 (4H, b) |
| 45 | 4-Cl | H | —CH(CH$_3$)— | MSA | 162–164 | 3300, 3150, 1745 1670, 1187 | |
| 46 | H | H | —CH(C$_6$H$_5$)— | MSA | 247–249 | 3400–3000, 2900 1745, 1670, 1200 1135, 690, 540, 520 | 0.67–2.43 (10H, m), 2.52 (3H, S), 3.43–3.97 (2H, m), 7.20–8.77 (11H, m), 9.18–9.93 (4H, b) |
| 47 | H | H | —CH$_2$CH$_2$— | MSA | 148–150 | 3300, 3100, 1750 1670, 1200 | 2.57 (3H, S), 3.07 (4H, S), 7.37 (5H, S), 7.57–8.74 (6H, m), 9.34–10.07 (4H, b) |
| 48 | 4-CH$_3$ | H | —CH$_2$CH$_2$— | MSA | 180–183 | 3350, 3150, 1750, 1680, 1225 | |
| 49 | 3-OCH$_3$ | 4-OCH$_3$ | —CH$_2$CH$_2$— | MSA | 129–134 | 3300, 3100, 1745 1670, 1630 | 2.47 (3H, S), 2.93 (4H, S), 3.73 (6H, S), 6.86–8.59 |

TABLE 5-continued

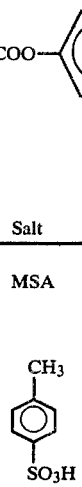

| Compound No. | R₁ | R₂ | Z | Salt | M.p. (°C.) | IR $\nu_{max}^{KBr}$ cm⁻¹ | NMR (DMSO—d₆) δ |
|---|---|---|---|---|---|---|---|
| 50 | 4-OCOCH₃ | H | —CH₂CH₂— | MSA | 144–147 | 3250, 3100, 1750, 1730 (Sh), 1500, 1320 | (9H, m), 9.09–9.76 (4H, b) 2.30 (3H, S), 2.50 (3H, S), 3.07 (4H, S), 7.23–8.36 (10H, m), 8.86–9.63 (4H, m) |
| 51 | 4-NH₂ | H | —CH₂CH₂— | 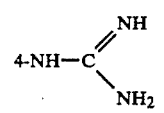 | 162–165 | 3350, 3100, 1745 1675, 1200 | 2.27 (3H, S), 2.90 (4H, S), 6.60–8.63 (16H, m), 9.06–9.89 (4H, b) |
| 52 | 4-NH—C(=NH)NH₂ | H | —CH₂CH₂— | 2MSA | 68–71 | 3300, 3150, 1740, 1670, 1520, 1200 | 2.53 (6H, S), 3.06 (4H, S), 7.17–8.64 (14H, m), 9.17–9.70 (4H, b), 9.87 (1H, S) |
| 53 | 4-NH—C(=NH)NH₂ | H | —CH₂CH(CH₂CH₃)— | 2MSA | 120–123 | 3300, 3150, 1740 (Sh) 1670, 1200 | 1.30 (3H, t⁽⁸⁾), 2.40–2.83 (8H, b), 3.77 (2H, m), 7.33–8.70 (20H, m), 9.20–9.83 (4H, b), 10.16 (1H, S) |
| 54 | H | H | —CH₂CH₂CH₂— | MSA | 164–170 | 3550–2900, 1745 1660, 1210, 1150 700 | 1.73–2.47 (2H, m), 2.70 (3H, S), 2.50–3.07 (2H, m), 7.08–8.57, (11H, m), 8.67–9.57 (4H, b) |
| 55 | 4-NO₂ | H | —CH₂CH₂CH₂— | MSA | 158–160 | 3250, 3080, 1755 1680, 1342 | 1.87–3.10 (6H, m), 2.47 (3H, S), 7.33–8.67 (10H, m), 9.00–9.67 (4H, b) |
| 56 | 4-NHCOCH₃ | H | —CH₂CH₂CH₂— | MSA | 153–155 | 3255, 3150, 1755 1680, 1660 | |
| 57 | H | H | —CH=CH— | MSA | 229–232 | 3350, 3150, 1730 1680 | |
| 58 | 4-CH₃ | H | —CH=CH— | MSA | 176–181 | 3350, 3150, 1720 1675, 1625, 1230 | 2.40 (3H, S), 2.43 (3H, S), 7.03–8.90 (12H, m), 9.37–10.04 (4H, b) |
| 59 | 3-OCH₃ | 4-OCH₃ | —CH=CH— | MSA | 208–212 | 3350, 3100, 1710 (Sh) 1670, 1620, 1270 | 2.57 (3H, S), 3.90 (6H, S), 6.73–8.66 (11H, m), 10.54–11.21 (4H, b) |
| 60 | 4-OCOCH₃ | H | —CH=CH— | MSA | 232–236 | 3300, 3100, 1750 (Sh) 1730, 1670, 1500, 1370 | |
| 61 | 2-Cl | H | —CH=CH— | MSA | 198–201 | 3350, 3150, 1715 1670, 1520, 1200 | 2.53 (3H, S), 6.93–8.66 (12H, m), 9.16–9.76 (4H, b) |
| 62 | 4-NO₂ | H | —CH=CH— | 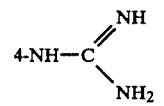 | 240–245 | 3350, 3150, 1720 1680, 1510, 1340, 1200 | |
| 63 | 4-NH₂ | H | —CH=CH— | 2MSA | 57–60 | 3350, 3100, 1720, 1670, 1630, 1500 1200 | 2.47 (6H, S), 6.7–8.6 (12H, m), 9.17–9.64 (4H, b) |
| 64 | 4-NH—C(=NH)NH₂ | H | —CH=CH— | 2MSA | 162–164 | 3300, 3150, 1720 (Sh), 1670, 1625, 1200 | 2.53 (6H, S), 6.80–8.63 (16H, m), 9.13–9.83 (4H, b), 10.13 (1H, S) |
| 65 | 4-NH—C(=NH)NH₂ | H | —CH=C(C₂H₅)— | 2MSA | 175–178 | 3300, 3150, 1720 (Sh), 1670, 1200 | 1.30 (3H, t), 2.67–3.00 (8H, b), 7.33–8.70 (15H, m) 9.17–9.80 (4H, b), 10.17 (1H, S) |
| 66 | 3-CF₃ | H | —CH=CH— | MSA | 154– | 3350, 3150, 1720 | 2.50 (3H, S), 7.08–8.63 |

TABLE 5-continued

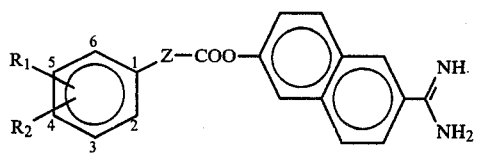

| Compound No. | R₁ | R₂ | Z | Salt | M.p. (°C.) | IR $\nu_{max}^{KBr}$ cm⁻¹ | NMR (DMSO—d₆) δ |
|---|---|---|---|---|---|---|---|
| 67 | H | H | —O—CH₂— | MSA | 158 | 1670, 1330 | (12H, m), 9.06–9.83 (4H, b) |
| 68 | 2-OCH₃ | H | —O—CH₂— | MSA | 168–170 | 3330, 3120, 1764, 1175 | |
| 69 | 4-Cl | H | —O—CH₂— | MSA | 149–151 | 3150, 1780, 1675 | |
| 70 | 2-Cl | 4-Cl | —O—CH₂— | MSA | 180–181 | 3150, 1769, 1670 | |
| 71 | 2-NO₂ | H | —O—CH₂— | MSA | 182–185 | 3420, 3350, 3080, 1783, 1680 | |
| 72 | 3-NO₂ | H | —O—CH₂— | MSA | 193–195 | 3440, 3070, 1782, 1356 | |
|  |  |  |  |  | 179–180 | 3300, 3100, 1772, 1675, 1350 | |
| 74 | 2-NH—(phenyl)-CF₃ | H | — | MSA | 147–149 | 3300, 3150, 1685, 1580, 1520, 1450, 1330 | 2.53 (3H, S), 6.97–8.70 (15H, m), 8.83–9.60 (4H, b) |
| 75 | 2-NH—(phenyl)(CH₃)(CH₃) | H | — | MSA | 159–162 | 3250, 3150, 1670, 1620, 1500, 1200 | 2.10 (3H, S), 2.27 (3H, S), 2.50 (3H, S), 6.67–8.80 (14H, m), 9.10–9.77 (4H, b) |

Note:
⁽¹⁾MSA = CH₃SO₃H
⁽²⁾S = singlet
⁽³⁾m = multilet
⁽⁴⁾b = broad
⁽⁵⁾Sh = shoulder
⁽⁶⁾TFA = measured in CF₃COOH
⁽⁷⁾d = doublet
⁽⁸⁾t = triplet

What is claimed is:

1. 6-Amidino-2-naphthyl 4-guanidinobenzoate and a pharmaceutically acceptable acid addition salt thereof.

* * * * *